United States Patent
Blacker et al.

(10) Patent No.: US 7,022,876 B2
(45) Date of Patent: Apr. 4, 2006

(54) PREPARATION OF MANDELIC ACID DERIVATIVES

(75) Inventors: Andrew John Blacker, Huddersfield (GB); Ian Nicholas Houson, Huddersfield (GB)

(73) Assignee: Avecia Ltd., Manchester (GB)

( * ) Notice: Subject to any disclaimer, the term of this patent is extended or adjusted under 35 U.S.C. 154(b) by 56 days.

(21) Appl. No.: 10/467,103

(22) PCT Filed: Feb. 15, 2002

(86) PCT No.: PCT/GB02/00667

§ 371 (c)(1),
(2), (4) Date: Aug. 5, 2003

(87) PCT Pub. No.: WO02/066410

PCT Pub. Date: Aug. 29, 2002

(65) Prior Publication Data

US 2004/0068140 A1   Apr. 8, 2004

(30) Foreign Application Priority Data

Feb. 16, 2001   (GB) .................................. 0103857

(51) Int. Cl.
*C07C 59/48*   (2006.01)
*C07C 59/00*   (2006.01)
(52) U.S. Cl. ...................... 562/470; 562/465
(58) Field of Classification Search ................. 562/470, 562/465
See application file for complete search history.

(56) References Cited

U.S. PATENT DOCUMENTS 5,223,416 A   6/1993   Endo et al. .................. 435/128

FOREIGN PATENT DOCUMENTS

WO   02/10095   2/2002

OTHER PUBLICATIONS

Belokon et al, Organic Letters, 2(11), pp1617-1619 (2000).*
Xiang-Ge et al , J. Chem. Soc. Dalton Trans, pp3303-3309 (1999).*
Yaozhong et al, Tetrahedron Letter, 53(42) pp 143237-14338.*
Yaozhong et al, Tetrahedron Asymmetry vol. 6(12) pp2915-2916.*

Yaozhong, Jiang, et al., "Salen-Ti(OR)₄ Complex Catalysed Trimethylsilylcyanation of Aldehydes", Tetrahedron, vol. 53, No. 42, pp. 14327-14338, 1997.
Yaozhong, Jiang, et al., "Asymmetric Synthesis XXVII: Asymmetric Catalytic Trimethylsilylcyanation of Aldehydes by Novel Ti-Chiral Schiff Base Complexes", Tetrahedron: Asymmetry, vol. 6, No. 12, pp. 2915-2916, 1995.
Belokon, Yuri N., et al, "Vanadium-Catalyzed Asymmetric Cyanohydrin Synthesis", Organic Letters 2000, vol. 2, No. 11, pp. 1617-1619, 2000.
Zhou, Xiang-Ge, et al, "Titanium and ruthenium binaphthyl Schiff base complexes as catalysts for asymmetric trimethylsilylcyanation of aldehydes", J. Chem. Soc., Dalton Trans., 1999, pp. 3303-3309.
Belokon et al, J. Am. Chem. Soc., 121(16):3968-3973 (1999).
Mori et al, Comprehensive Asymmetric Catalysis II, Chapter 28; Ed. Jacobsen, Pfaltz, Yamamoto.

* cited by examiner

Primary Examiner—J. Parsa
(74) Attorney, Agent, or Firm—Morgan Lewis & Bockius LLP

(57) ABSTRACT

A process is provided for the preparation of mandelic acid derivatives. The process comprises the steps of:
  (a) stereoselectively cyanating a compound of Formula (2) to yield the corresponding cyanohydrin;

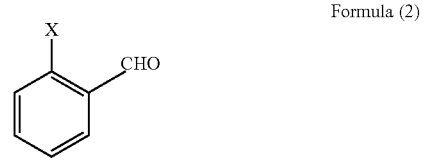

Formula (2)

(b) hydrolyzing the product of step (a) to the corresponding compound of Formula (1).

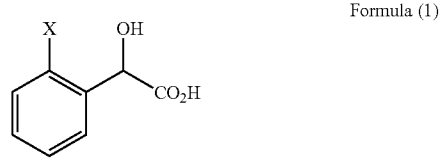

Formula (1)

wherein X is a substituent.

9 Claims, No Drawings

PREPARATION OF MANDELIC ACID DERIVATIVES

This invention relates to processes for the preparation of chiral forms of ortho substituted mandelic acid.

Mandelic acid substituted in the ortho position is a key intermediate in the synthesis of pharmaceuticals in particular anticoagulants such as clopidogrel.

A number of different processes for the preparation of enantiomers of mandelic acid have been proposed. For example in U.S. Pat. No. 5,223,416 a biological process is described which involves subjecting (R),(S)-benzaldehyde cyanohydrin, or a derivative, or a mixture of prussic acid and benzaldehyde to the action of a microorganism. However, the process most commonly used is based on selectively forming the (R) or (S) enantiomers of the corresponding cyanohydrin and then hydrolysing to yield the desired 2-hydroxy acid with no loss of stereochemical purity.

Many methods for the asymmetric addition of cyanating agents to aryl aldehydes have been reported in the literature. These methods are reviewed in Comprehensive Asymmetric Catalysis; Eds. Jacobsen, E. N., Pfaltz, A. and Yamamoto, H; Chapter 28. High enantiomeric excesses (e.e.) of one or other enantiomer of cyanohydrin have been achieved with enzyme and peptide-catalysts. However, with non-biological catalysts much lower optical yields are seen. These methods also generally involve the use of high levels of catalyst (i.e. more than 5 mol % catalyst).

Two recent papers (Journal of the American Chemical Society, 1999, 121, 3968–3973; and Organic Letters, 2000, 2, 1617–1619) describe new titanium and vanadium chiral catalysts respectively which are able to convert aryl aldehydes at ambient temperature (or lower) into the corresponding trimethylsilyl ethers of cyanohydrins at high yield and optical purity using low levels of catalyst. While these methods are of general applicability they give products of lower optical purity with ortho substituted benzaldehydes, especially those where the aldehyde is electron deficient.

According to the present invention there is provided a process for the stereoselective preparation of a compound of Formula (1):

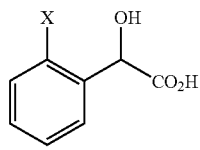

Formula (1)

wherein:
X is a substituent:
comprising the steps:
(a) stereoselectively cyanating a benzaldehyde of Formula (2) to yield the corresponding cyanohydrin

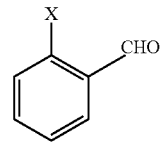

Formula (2)

wherein:
X is a substituent: and
(b) hydrolysing the product of step (a) to the corresponding compound of Formula (1).

It is preferred that X is a halogen, more preferably Cl or Br and especially Cl.

The cyanating agent used in step (a) is preferably a mixture of a compound of formula YCN and trimethylsilylchloride (TMSCl); a mixture of YCN and acetic anhydride wherein Y is H or an alkali, alkaline earth or transition metal, or trimethylsilylcyanide (TMSCN) optionally with a Lewis acid.

Preferably the cyanating agent is TMSCN.

A stereospecific catalyst may be used in step (a).

Preferred stereospecific catalysts are of Formula (3), Formula (4), Formula (5) or Formula (6) or mixtures of catalysts of Formula (3) and Formula (5) or Formula (4) and Formula (6):

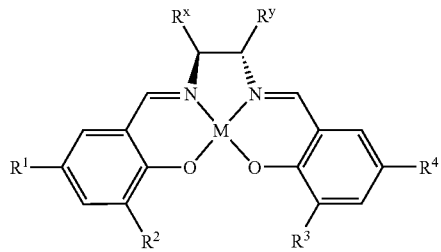

Formula (3)

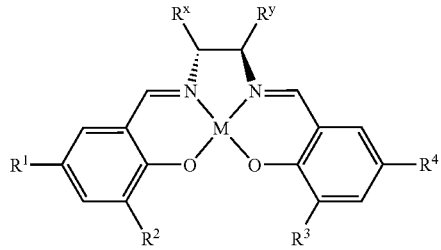

Formula (4)

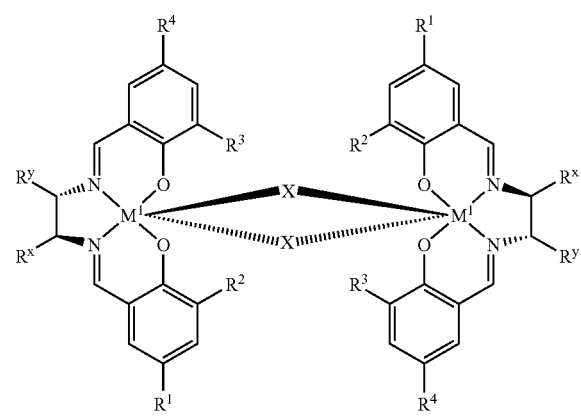

Formula (5)

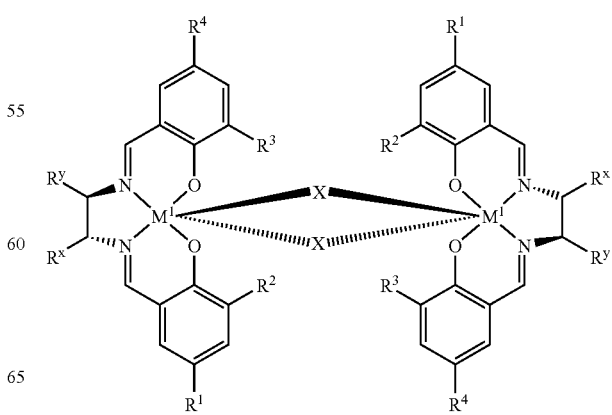

Formula (6)

wherein:
M is a transition metal complex preferably selected from the group consisting of V=O, V(OH), V(OH)$_2$, V(OR$^5$), V(OR$^5$)$_2$, VCl, VBr, VCl$_2$, VBr$_2$, Ti(OH)$_2$, Ti(CN)$_2$, TiCl$_2$, TiBr$_2$, Ti(OR$^5$)$_2$, ZrCl$_2$, Cr, WCl, MnCl, FeCl, ReO, RuO, wherein R$^5$ is C$_{1-6}$-alkyl;

each M$^1$ independently is a transition metal selected from the group consisting of V, Ti, Zr, Cr, W, Mn, Fe, Re and Ru;

X is O, S or a halogen;

R$^1$, R$^2$, R$^3$ and R$^4$ are each independently H, optionally substituted C$_{1-16}$-alkyl, C$_{1-16}$-alkoxy, halogen or nitro; and R$^x$ and R$^y$ each independently are H, optionally substituted C$_{1-16}$-alkyl, optionally substituted aromatic or heteroaromatic rings or R$^x$ and R$^y$ together represent an aliphatic, aromatic or heteroaromatic ring system.

Preferably in the catalyst of Formulae (3), (4), (5) and (6) at least one of R$^1$, R$^2$, R$^3$ and R$^4$ is C$_{1-4}$-alkyl and more preferably at least one of R$^1$, R$^2$, R$^3$ and R$^4$ is t-butyl. It is especially advantageous if in the catalyst of Formulae (3), (4), (5) and (6) R$^1$, R$^2$, R$^3$ and R$^4$ are all t-butyl.

Preferably in Formulae (3), (4), (5) and (6) R$^x$ and R$^y$ together represent an optionally substituted aliphatic ring system, especially an optionally substituted C$_{3-6}$ aliphatic ring system, or R$^x$ and R$^y$ together represent optionally substituted phenyl.

In Formula (3) and Formula (4) M is preferably V=O, V(OH), V(OH)$_2$, V(OR$^5$), V(OR$^5$)$_2$, TiCl$_2$, TiBr$_2$, Ti(OR$^5$)$_2$, ZrCl$_2$, Cr, MnCl, FeCl, wherein R$^5$ is C$_{1-6}$-alkyl more preferably M is TiCl$_2$, TiBr$_2$, V(OH), V(OH)$_2$, V(OR$^5$) or V=O, especially V=O or V(OH).

The catalyst of Formula (3) and Formula (4) may have an additional ligand. Preferably, these ligands comprise optionally substituted aliphatic, aromatic or heteroaromatic diols able to ligate to the metal in the catalyst of Formula (3) and Formula (4) through the diols.

In the catalysts of Formula (5) and (6) each M$^1$ is preferably a different transition metal.

Preferably in Formula (5) and Formula (6) each M$^1$ independently is Ti or V.

In step (a) a catalyst of Formula (3) and/or Formula (5) may be used to yield the (R) enantiomer as the major product and a catalyst of Formula (4) and/or Formula (6) may be used to yield the (S) enantiomer as the major product.

The catalysts of Formulae (3), (4), (5) and (6) may be prepared using the procedures described in Journal of the American Chemical Society, 1999, 121, 3968–3973; and Organic Letters, 2000, 2, 1617–1619 the methods of which are incorporated herein by reference.

It is believed that in step (a) the catalysts of Formula (3) and Formula (4) may exist in tautomeric forms other than those shown in this specification. In particular they may form dimers, including those of Formula (5) and Formula (6), and other multiple forms (for example see FIG. 2 of Journal of the American Chemical Society, 1999, 121, 3968–3973 and Scheme 1 of Organic Letters, 2000, 2, 1617–1619). These tautomers are included within the scope of the present invention.

In many embodiments it is preferred that in step (a) the molar ratio of cyanating agent to compound of Formula (2) is in the range of from 0.9:1 to 10:1, preferably 1:1 to 5:1.

Preferably the product of step (a) is produced in greater than 60% enantiomeric excess (e.e.) and more preferably in greater than 65% e.e. It is especially preferred that the product of step (a) is produced in greater than 70% e.e., more especially greater than 75% e.e. and particularly greater than 80% e.e.

Step (a) of the process can be performed in the presence of organic solvent which is unreactive towards the reagents employed. Examples of suitable solvents include halocarbons, especially chlorocarbons such as dichloromethane, chloroform, dichloroethane, chlorobenzene, ethers, particularly C$_{1-6}$ alkylethers such as t-butyl methyl ether, tetrahydrofuran, dimethylformamide, acetonitrile, alcohols such as t-butanol, nitrogen containing heterocycles such as 2,6-lutidine, toluene and mixtures thereof. Preferably the solvent is dichloromethane, chlorobenzene, t-butanol, 2,6-lutidine, toluene, t-butyl methyl ether or mixtures thereof. More preferably the solvent is dichloromethane, t-butanol, 2,6-lutidine or mixtures thereof.

When M in Formula (3) and Formula (4) is TiCl$_2$ or TiBr$_2$ then it is preferred that step (a) of the process is not carried out under anhydrous conditions.

Steps (a) and (b) may also be performed in a continuous process. In a preferred continuous process the catalyst of Formulae (3), (4), (5) or (6) is immobilised on a solid support. The catalyst of Formulae (3), (4), (5) and (6) may be immobilised using techniques well known to those skilled in the art.

The solid support may be selected from, for example, spherical polymer beads (either macro or microporous), inorganic particles (silica, ion exchange resins, zeolites), membranes, films and composite structures.

Techniques commonly used to immobilize a soluble substance within or on an insoluble matrix material include: encapsulation; covalent attachment of a substance to a preformed crosslinked insoluble polymer matrix; or covalent attachment of a substance to a preformed linear polymer.

Step (a) of the process is preferably performed at a temperature in the range of from −20° C. to 50° C. and more preferably in the range of from −5° C. to 30° C. It is especially preferred that step (a) is carried out at a temperature in the range of from 0° C. to 25° C.

Step (a) of the process is advantageously allowed to proceed to at least 90% conversion.

The reaction time of step (a) of the process of the present invention will depend on a number of factors, for example the reagent concentrations, the stirring rate, the relative amounts of reagents and particularly the reaction temperature. Typical reaction times, in addition to the reagent addition times, range from 0.5 hour to 48 hours, with reaction times of 1 to 20 hours being common. When the reaction is carried out at ambient temperature, reaction times of from 2 to 18 hours are often employed.

In step (b) of the process hydrolysis is preferably carried out by contact with an aqueous mineral acid such as HCl. Preferably the mineral acid concentration is greater than 1M and more preferably greater than 5M. Step (b) may be carried out by heating the reaction mixture until hydrolysis is complete, for example for 1 to 48 hours at temperatures from 50 to 110° C.

The product of step (b) may be further purified by crystallisation. The crystallisation is preferably a stereospecific crystallisation.

Crystallisation is preferably carried out in the presence of a solvent. Preferred solvents are alcohols such as methanol, ethanol, propan-1-ol, propan-2-ol, n-butanol, sec-butanol, tert-butanol, ethers such as tert-butylmethylether and tetrahydrofuran, alkanes such as n- or iso-pentane, n- or iso-hexane, cyclohexane, heptane or octane, aromatic solvents such as toluene or xylene or chlorinated solvents such as dichlormethane or chlorobenzenee or a mixture thereof.

Preferably the product of the crystallisation is produced in greater than 80% enantiomeric excess (e.e.) more preferably in greater than 85% e.e., it is especially preferred that the product of step (a) is produced in greater than 90% e.e. and more especially in greater than 95% e.e.

Advantageously the crystallisation mixture is seeded with a crystal of the desired enantiomer of the compound of Formula (1). Preferably the crystal used to seed the crystallisation mixture is more than 95% pure. More preferably it is more than 99% pure.

The crystallisation may be repeated 2 or more times to yield material of the desired purity.

The product of step (a) may be isolated prior to step (b). However, preferably the product of step (a) is used in step (b) without any further processing or purification.

A preferred embodiment of the present process is a process for the stereoselective preparation of a compound of Formula (1), as hereinbefore defined, comprising the steps:
(a) reacting a compound of Formula (2), as defined hereinbefore, with a mixture of a compound of formula YCN and trimethylsilylchloride (TMSCl), wherein Y is H or an alkali, alkaline earth or transition metal, or trimethylsilylcyanide (TMSCN), optionally with a Lewis acid, in the presence of a catalyst of Formula (3) or Formula (5) to yield the (R) enantiomer of the trimethylsilyl ether of the corresponding cyanohydrin or in the presence of a catalyst of Formula (4) or Formula (6) to yield the (S) enantiomer of the trimethylsilyl ether of the corresponding cyanohydrin;

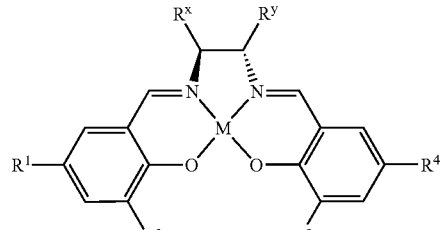

Formula (3)

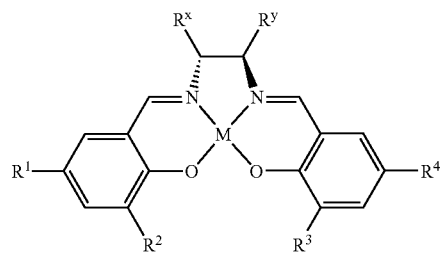

Formula (4)

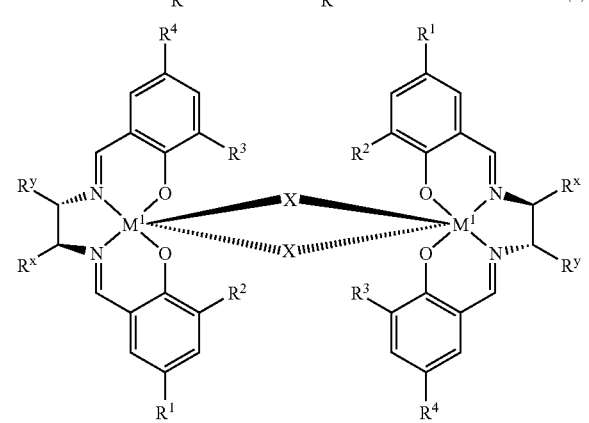

Formula (5)

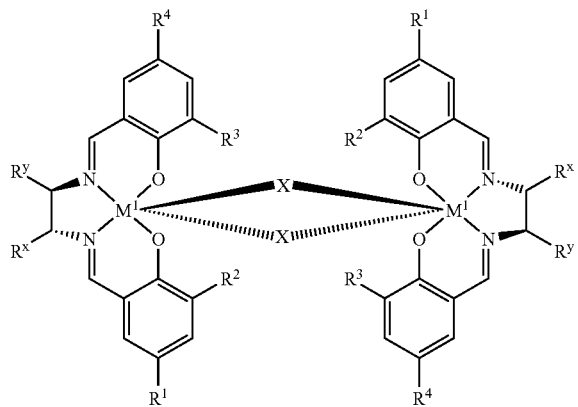

Formula (6)

wherein:
M is a transition metal complex;
each $M^1$ independently is a transition metal selected from the group consisting of V, Ti, Zr, Cr, W, Mn, Fe, Re and Ru;
X is O, S or a halogen;
$R^1$, $R^2$, $R^3$ and $R^4$ are each independently H, optionally substituted $C_{1-16}$-alkyl, $C_{1-16}$-alkoxy, halogen or nitro; and
$R^x$ and $R^y$ each independently are H, optionally substituted $C_{1-16}$-alkyl, optionally substituted aromatic or heteroaromatic rings or $R^x$ and $R^y$ together represent an aliphatic, aromatic or heteroaromatic ring system; and
(b) hydrolysing the product from step (a) to the corresponding compound of Formula (1).

Preferably in Formula (3) and Formula (4) M is transition metal complex selected from the group consisting of V=O, V(OH), V(OH)$_2$, V(OR$^5$), Ti(OR$^5$)$_2$, VCl, VBr, VCl$_2$, VBr$_2$, Ti(OH)$_2$, Ti(CN)$_2$, TiCl$_2$, TiBr$_2$, Ti(OR$^5$)$_2$, ZrCl$_2$, Cr, WCl, MnCl, FeCl, ReO, RuO, wherein $R^5$ is $C_{1-6}$-alkyl.

A more preferred embodiment of the present process is a process for the preparation of (R)-chloromandelic acid comprising the steps:
(a) reacting 2-chlorobenzaldehyde with trimethylsilylcyanide (TMSCN) in the presence of a catalyst of Formula (7) to yield (R)-2-chloromandelonitrile silyl ether;

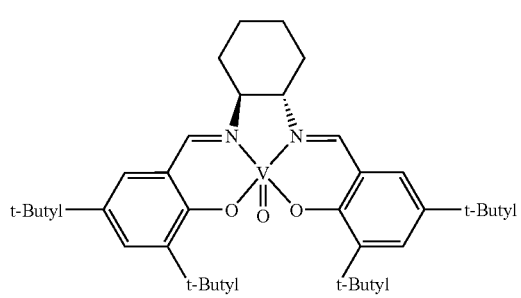

Formula (7)

(b) hydrolysing the product from step (a) to yield (R)-2-chloromandelic acid; and
(c) purifying the product from step (b) by means of a stereospecific crystallisation, wherein the crystallisation mixture is seeded with crystals of (R)-2-chloromandelic acid of greater than 99% purity.

The invention is further illustrated below wherein all parts and percentages are by weight unless otherwise stated.

EXAMPLE 1

Step 1(a)

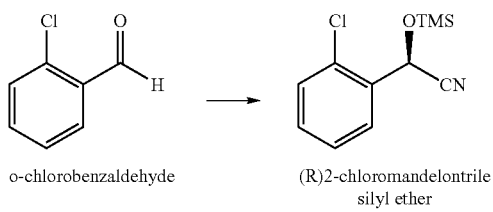

o-chlorobenzaldehyde         (R)2-chloromandelontrile
                                silyl ether o-Chlorobenzaldehyde (0.459 g, 0.37 ml, 3.269 mmol) was added by a syringe to a catalyst of Formula (7) ((2 mg, $3.3 \times 10^{-3}$ mmol) in $CH_2Cl_2$ (5 ml), followed by TMSCN (0.357 g, 0.48 ml, 3.597 mmol). The solution was stirred at room temperature overnight at 20° C. Analysis by G.C. showed that the reaction had gone to 92% conversion (76% e.e.) after 18 hrs and 96% conversion (76% e.e.) after 48 hrs. The catalyst was removed by passing the mixture through a plug of silica and washing with dichloromethane.

Step 1(b)

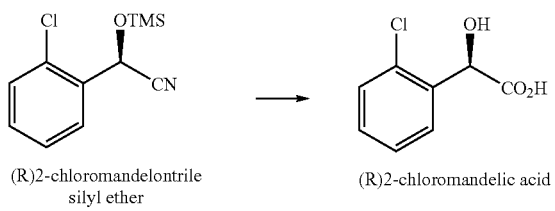

(R)2-chloromandelontrile         (R)2-chloromandelic acid
   silyl ether

The silyl ether of 2'-chloromandelonitrile (0.39 g, 1.626 mmol) from step 1(a) and water (0.5 ml) were placed in a 100 ml flask equipped with a reflux condenser. Hydrochloric acid (37%, 5 ml) was added via a dropping funnel and the solution was stirred and heated to 80° C. for 48 hrs. The solution was cooled to room temperature and diethyl ether (10 ml) was added. After vigorous stirring for 30 mins the stirrer was stopped. The extent of reaction was determined by conversion of the (R) 2-chloromandelic acid to the corresponding methyl ester. A 0.2 ml sample was taken into methanol (1 ml) in a G.C. vial and left to stand at ambient temperature for 1 hr to form the methyl ester. The methyl ester was determined by G.C. analysis which showed 100% conversion to with no trace of starting material indicating that the reaction had gone to completion after 48 hrs. Optical purity of the final product was determined by G.C. analysis following conversion to the trifluoroacetate ester. The analysis showed that the reaction had gone with stereochemical retention.

The product was extracted from the reaction mixture with diethyl ether (3×20 ml), purified by passing through a plug of silica, dried using $MgSO_4$ and concentrated.

Step 1(c)

The crude (R) 2-chloromandelic acid from step 1(b) was heated in toluene until dissolved and seed crystals of pure (R)-2-chloromandelic acid were added. The solution was gradually cooled to ambient temperature, over which time crystallisation occurred. The crystals were collected using a Buchner funnel/filter system. The crystallisation process was repeated in order to obtain crystals with >99% e.e. (analysed as the trifluoroacetate ester by G.C.).

EXAMPLE 2

Step 2(a)

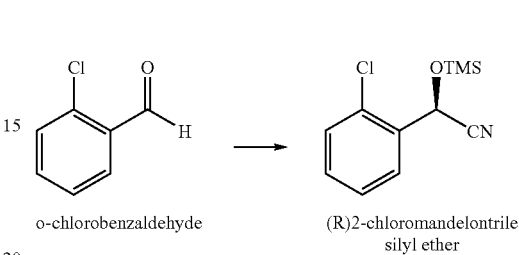

o-chlorobenzaldehyde         (R)2-chloromandelontrile
                                silyl ether o-Chlorobenzaldehyde (2.00 g, 1.62 ml, 14.23 mmol) was added to a vanadium catalyst of Formula (7) (8.7 mg, $1.42 \times 10^{-2}$ mmol) in $CH_2Cl_2$ (20 ml), followed by TMSCN (1.41 g, 1.95 ml, 14.23 mmol). The solution was stirred at room temperature overnight at 20° C. Analysis by G.C. showed that the reaction had gone to 95% conversion (81% e.e.) after 1.5 hrs and to 97% conversion (81% e.e.) after 22 hrs. The catalyst was removed by passing the mixture through a plug of silica and washing with 10:1 v/v hexane: ethyl acetate.

Step 2(b)

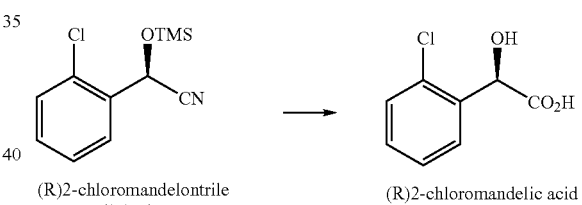

(R)2-chloromandelontrile         (R)2-chloromandelic acid
   silyl ether (R) 2-chloromandelonitrile silyl ether (0.39 g, 1.626 mmol) from step 2(a) and water (0.5 ml) were placed in a 100 ml flask equipped with a reflux condenser. Hydrochloric acid (37%, 5 ml) was added via a dropping funnel and the solution was stirred and heated to 80° C. for 5 hrs. The solution was cooled to room temperature and diethyl ether (10 ml) was added. After vigorous stirring for 30 mins the stirrer was stopped.

The extent of reaction was determined by conversion of the (R) 2-chloromandelic acid to the corresponding methyl ester. A 0.2 ml sample was taken into methanol (1 ml) in a G.C. vial and left to stand at ambient temperature for 1 hr to form the methyl ester. The methyl ester was determined by G.C. analysis which showed 100% conversion with no trace of starting material indicating that the reaction had gone to completion after 48 hrs.

Optical purity of the final product was determined by G.C. analysis following conversion to the trifluoroacetate ester. The analysis showed that the reaction had gone with stereochemical retention.

The product was extracted from the reaction mixture with diethyl ether (3×20 ml), purified by passing through a plug of silica, dried using $MgSO_4$ and concentrated.

Step 2(c)

The crude (R) 2-chloromandelic acid from step 2(b) was heated in toluene until dissolved and seed crystals of pure (R)-2-chloromandelic acid were added. The solution was gradually cooled to ambient temperature, over which time crystallisation occurred. The crystals were collected using a Buchner funnel/filter system. The crystallisation process was repeated in order to obtain crystals with >99% e.e. (analysed as the trifluoroacetate ester by G.C.).

EXAMPLE 3

Example of Step (a)

Preparation of (R) 2-chloromandelonitrile Silyl Ether

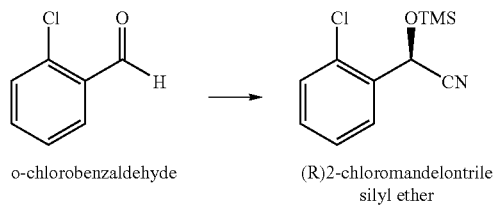

o-chlorobenzaldehyde                (R)2-chloromandelontrile
                                     silyl ether o-Chlorobenzaldehyde (1.00 g, 0.81 ml, 7.114 mmol) was added to a titanium dimer catalyst of Formula (8) (8.6 mg, $7.114 \times 10^{-3}$ mmol) in $CH_2Cl_2$ (9 ml)

Formula (8)

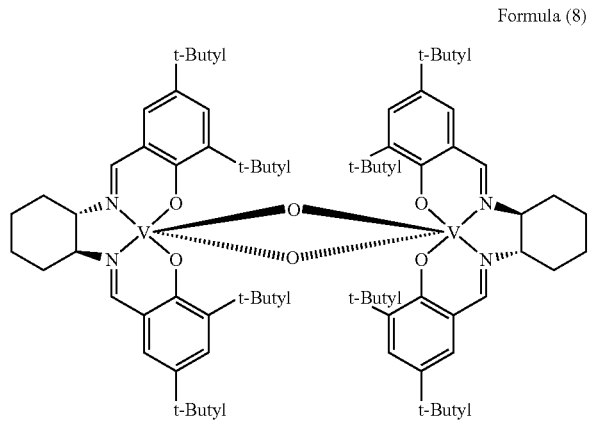

followed by TMSCN (0.776 g, 1.06 ml, 7.825 mmol). The solution was stirred at room temperature overnight at 20° C. Analysis by G.C. showed that the reaction had gone to 97% conversion (60% e.e.) after 1 hr and 97% conversion (59% e.e.) after 18 hrs. The catalyst was removed by passing the mixture through a plug of silica and washing with dichloromethane.

EXAMPLE 4

Example of Step (a)

Preparation of (S)-chloromandelonitrile Silyl Ether

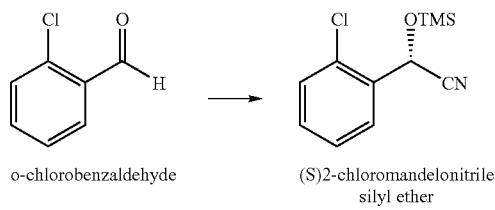

o-chlorobenzaldehyde                (S)2-chloromandelonitrile
                                     silyl ether o-Chlorobenzaldehyde (9.9 g, 8.0 ml, 70.43 mmol) was added to a vanadium catalyst of Formula (9) (43.5 mg, $7.11 \times 10^{-2}$ mmol) in $CH_2Cl_2$ (100 ml)

Formula (9)

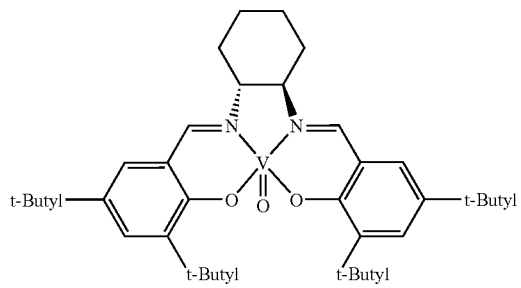

followed by TMSCN (6.90 g, 9.45 ml, 69.5 mmol). The solution was stirred at room temperature overnight at 20° C. Analysis by G.C. showed that the reaction had gone to 94% conversion (79% e.e.) after 25 hrs and 96% conversion (79% e.e.) after 44.5 hrs. The catalyst was removed by passing the mixture through a plug of silica and washing with dichloromethane.

EXAMPLE 5

Example of Step (a)

Preparation of (R) 2-chloromandelonitrile Acetate

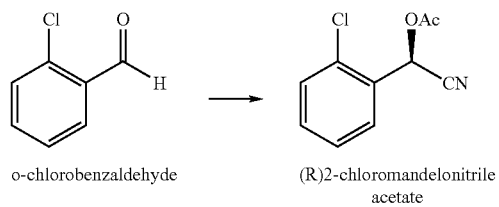

o-chlorobenzaldehyde                (R)2-chloromandelonitrile
                                     acetate o-Chlorobenzaldehyde (2.0 g, 1.62 ml, 14.23 mmol) was added via syringe to an agitated mixture of potassium cyanide (2.793 g, 43.8 mmol) and a vanadium catalyst* of Formula (7) (90 mg, $14.23 \times 10^{-2}$ mmol) in $CH_2Cl_2$ (55 ml), followed by 2,6-lutidine (0.147 g, 0.16 ml, 1.37 mmol) and water (0.25 g, 0.25 ml, 13.66 mmol). The slurry was cooled to a temperature of −6° C. and acetic anhydride (3.08 g, 2.85 ml, 30.17 mmol) was added via a syringe. The slurry was agitated at a temperature of −5° C. to 0° C. Analysis by G.C. showed that the reaction had gone to 51% conversion (62% e.e.) after 4 hrs and to 61% conversion (53% e.e.) after 7 hrs. The excess potassium cyanide was filtered off and the product was washed with dichloromethane before the filtrates were reduced in vacuo. The residues were dissolved in 10:2 v/v hexane:ethyl acetate and the catalyst was removed by passing the mixture through a bed of silica and washing with 10:1 v/v hexane:ethyl acetate.

EXAMPLE 6

Example of Step (a)

Preparation of (R) 2-chloromandelonitrile Acetate

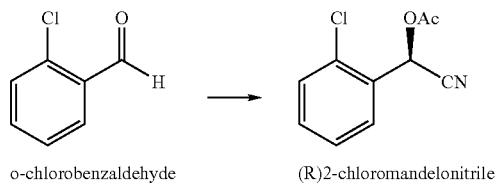

o-chlorobenzaldehyde → (R)2-chloromandelonitrile acetate o-Chlorobenzaldehyde (1.0 g, 0.82 ml, 7.11 mmol) was added via syringe to an agitated mixture of potassium cyanide (1.85 g, 28.46 mmol) and a titanium dimer catalyst of Formula (8) (72.8 mg, 0.06 mmol) in $CH_2Cl_2$ (18 ml), followed by t-butanol (0.56 g, 0.72 ml, 7.49 mmol). The slurry was cooled to a temperature of −5° C. and acetic anhydride (2.905 g, 2.68 ml, 28.46 mmol) was added via a syringe. The slurry was agitated at a temperature of −5° C. to 0° C. Analysis by G.C. showed that the reaction had gone to 31% conversion (49% e.e.) after 4 hrs and to 33% conversion (51% e.e.) after 5.75 hrs.

EXAMPLE 7

Example of Step (a)

Preparation of (S) 2-chloromandelonitrile Acetate

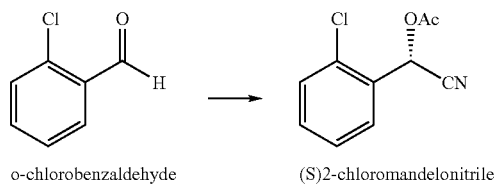

o-chlorobenzaldehyde → (S)2-chloromandelonitrile acetate o-Chlorobenzaldehyde (2.0 g, 1.62 ml, 14.23 mmol) was added via syringe to an agitated mixture of potassium cyanide (2.793 g, 43.8 mmol) and a vanadium catalyst of Formula (9) (87 mg, 14.23×10$^{-2}$ mmol) in $CH_2Cl_2$ (55 ml), followed by 2,6-lutidine (0.147 g, 0.16 ml, 1.37 mmol) and water (0.25 g, 0.25 ml, 13.66 mmol). The slurry was cooled to a temperature of 0° C. and acetic anhydride (3.08 g, 2.85 ml, 30.17 mmol) was added via a syringe. The slurry was agitated at a temperature of −5° C. to 0° C. Analysis by G.C. showed that the reaction had gone to 65% conversion (81% e.e.) after 1.5 hrs and to 94% conversion (79% e.e.) after 5 hrs. The excess potassium cyanide was filtered off and the product was washed with dichloromethane before the were filtrates reduced in vacuo. The residues were dissolved in 10:2 v/v hexane:ethyl acetate and the catalyst was removed by passing the mixture through a bed of silica and washing with 10:1 v/v hexane:ethyl acetate.

The compounds of Examples 3 to 7 are hydrolysed to the corresponding mandelic acids using conditions analogous to Steps 1 (b) and 2(b) above.

The invention claimed is:

1. A process for the catalytic and stereospecific preparation of a compound of Formula (1):

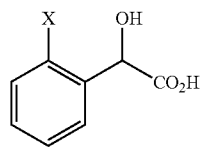

Formula (1)

wherein:
X is chlorine:
comprising the steps:
(a) stereoselectively cyanating a benzaldehyde of Formula (2)

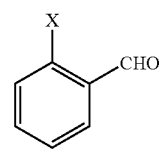

Formula (2)

wherein:
X is chlorine in the presence of a catalyst of Formula (3), (4), (5) or (5)

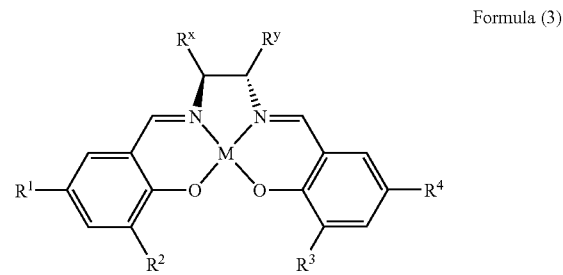

Formula (3)

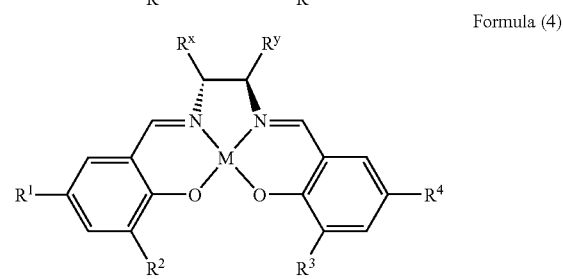

Formula (4)

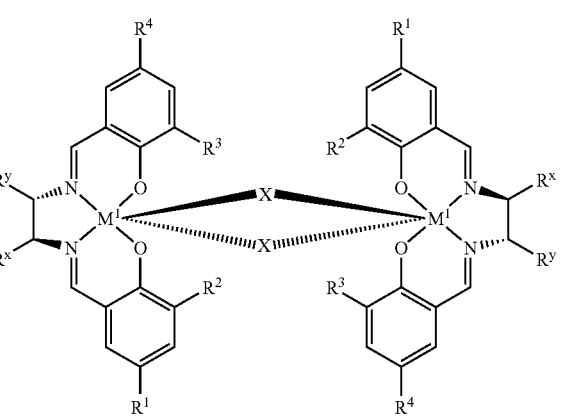

Formula (5)

Formula (6)

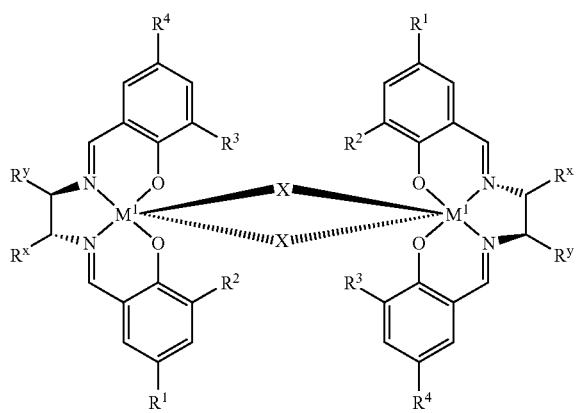

wherein:
M is V=O
each $M^1$ is V;
$R^1$, $R^2$, $R^3$ and $R^4$ are t-butyl; and
$R^x$ and $R^y$ together represent cyclohexyl ring system,
to yield the corresponding cyanohydrin, and
(b) hydrolysing the product of step (a) to the corresponding compound of Formula (1).

2. A process according to claim 1 wherein in step (a) the cyanating agent is TMSCN.

3. A process according to claim 1 or 4 where in step (b) the product of step (a) is hydrolysed by contact with aqueous mineral acid.

4. A process according to claim 3 where in step (b) the mineral acid is HCl.

5. A process according to claim 1 for the preparation of a compound of Formula (1) comprising the steps:
(a) reacting a compound of Formula (2) with a mixture of a compound of formula YCN and trimethylsilylchloride (TMSCl), wherein Y is H or an alkali, alkaline earth or transition metal, or trimethylsilylcyanide (TMSCN), optionally with a Lewis acid, in the presence of a catalyst of Formula (3) or Formula (5) to yield the (R) enantiomer of the trimethylsilyl ether of the corresponding cyanohydrin or in the presence of a catalyst of Formula (4) or Formula (6) to yield the (S) enantiomer of the trimethylsilyl ether of the corresponding cyanohydrin
(b) hydrolysing the product from step (a) to the corresponding compound of Formula (1).

6. A process according to claim 5 where in step (a) the catalyst is of Formula (3).

7. A process according to claim 1 for the preparation of (R)-chloromandelic acid comprising the steps:
(a) stereoselectively reacting 2-chlorobenzaldehyde with trimethylsilylcyanide (TMSCN) in the presence of a catalyst of Formula (7) to yield (R)-2-chloromandelonitrile silyl ether;

Formula (7)

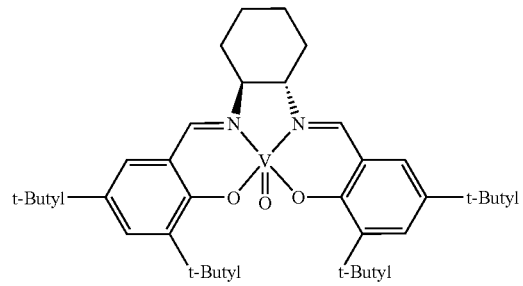

and
(b) hydrolysing the product from step (a) to yield (R)-chloromandelic acid.

8. A process according to any one of claim 1, 2, 5 or 6 wherein the catalyst of Formula (3) or (4) has an additional ligand.

9. A process according to claim 7 wherein the catalyst of Formula (7) has an additional ligand.

* * * * *